United States Patent
Masters et al.

(10) Patent No.: US 6,333,024 B1
(45) Date of Patent: Dec. 25, 2001

(54) EFFERVESCENT DUAL COMPONENT DENTIFRICE HAVING REDUCED SENSORY CUES

(75) Inventors: James G. Masters, Ringoes; David B. Viscio, Monmouth Jct.; Jeffrey H. Glaser; Gary Tambs, both of Belle Mead; Benjamin Y. Mandanas, Freehold, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/488,501

(22) Filed: Jan. 20, 2000

(51) Int. Cl.$^7$ ........................................ A61K 7/16
(52) U.S. Cl. ................................................ 424/49
(58) Field of Search .......................... 424/49–58

(56) References Cited

U.S. PATENT DOCUMENTS

| | | | |
|---|---|---|---|
| 4,487,757 | * 12/1984 | Kiozpeoplou | ......................... 424/44 |
| 4,528,180 | * 7/1985 | Schaeffer, I | ............................. 424/52 |
| 4,687,663 | * 8/1987 | Schaeffer, II | ........................... 424/52 |
| 4,849,213 | * 7/1989 | Schaeffer, III | .......................... 424/53 |

FOREIGN PATENT DOCUMENTS

| | | | |
|---|---|---|---|
| 0277400 | 8/1988 | (EP) | ............................... A61K/7/16 |
| 2186190 | 8/1987 | (GB) | ............................... A61K/7/16 |
| 97/02273 | * 1/1997 | (WO) . | |
| 9907335 | 2/1999 | (WO) | ............................... A61K/7/16 |

OTHER PUBLICATIONS

Patent Abstract of Japan, vol. 016, No. 049 and JP 03 251522 A Nov. 1991.

* cited by examiner

*Primary Examiner*—Shep K. Rose
(74) *Attorney, Agent, or Firm*—Paul Shapiro

(57) ABSTRACT

A two component effervescent dentifrice composition, having a first alkali metal bicarbonate containing component which also contains a naturally occurring alkyl vanillyamide such as capsaicin and a second acid-containing dentifrice component; the first and second components being separated prior to use, whereupon when combined upon application to the teeth the dentifrice provides an enhanced sensory signal.

12 Claims, No Drawings

EFFERVESCENT DUAL COMPONENT DENTIFRICE HAVING REDUCED SENSORY CUES

BACKGROUND OF THE INVENTION

1. Field of the Invention

The present invention relates to a two component effervescent dentifrice wherein upon mixing of the separate components during brushing, significantly enhanced consumer perceived sensory sensations are provided which instill in the consumer a perception of enhanced product cleaning performance.

2. The Prior Art

The addition of alkali metal bicarbonates to toothpaste for medicinal, general cleansing, or aesthetic purposes is known in the art. These bicarbonates are used as abrasives or polishing agents in dentifrice compositions providing moderate abrasion to remove debris and stained pellicle from tooth surfaces which are accessible to the toothbrush bristles.

Further, it is known that bicarbonate-acid mixtures in toothpaste compositions will create an effervescent effect and that such effervescent effect can provide certain sensory and tooth cleaning benefits. For example, U.S. Pat. No. 5,885,871 discloses a two component effervescent dentifrice composition wherein the effervescent signal produced by the dentifrice derives from the evolution of carbon dioxide upon the mixing of a high alkaline pH paste (pH range 8–9) and a low acid pH (pH 2–4) gel. Such dentifrice is comprised of a first alkali metal salt containing dentifrice component and a second acid-containing dentifrice component; the first and second components being separated prior to use; wherein, the pH of the two components when combined upon application to the teeth is between about 6.0 and about 7.1; whereby, the dentifrice provides enhanced removal of plaque growth and a tingly mouth feel.

There is an ongoing need for new and novel sensory benefits to promote the use of toothpaste, especially by children, for the benefits of such use as in cleaning of the tooth surfaces to remove plaque growth and the oral decay and disease associated therewith.

SUMMARY OF THE INVENTION

The present invention is directed to a two component effervescent dentifrice composition, having a first alkali metal bicarbonate containing dentifrice component and a second acid-containing dentifrice component; the first and second components being separated prior to use, wherein, the effervescent signal generated upon the combination and mixing of the components is enhanced by the presence in the combination of a naturally occurring alkyl vanillyamide, the presence of which provides a unique and consumer measurable sensation during brushing which instills in the consumer a perception of enhanced product cleaning performance.

DESCRIPTION OF THE PREFERRED EMBODIMENTS

An example of a naturally occurring alkyl vanillyamide is capsaicin, a trans-8-methyl-N-vanillyl-S nonenamide. Capsaicin is found in high concentration in fruit of plants of the Capsicum genus. Chili pepper, red pepper and paprika are all species of Capsicum. Capsicum is the dry powder obtained by grinding up the fruits of these plants. Capsicum oleoresin (or capsaicin oleoresin) is the liquid concentrate extracted from the dry powder. Capsaicin, a white crystalline material, is obtained from the liquid concentrate. Other examples of alkyl vanillyamides useful in the practice of the present invention include piperine, piperocaine and piperitone. Capsaicin is the preferred alkyl vanillyamide and is included in the dentifrice composition of the present invention in the range of about 0.001% to about 1.0% by weight and preferably about 0.05 ppm (parts per million) to about 3.5 ppm.

In the preparation of the effervescent dual component dentifrice composition of the present invention, the first component contains an alkali metal bicarbonate and the alkyl vanillyamide and the second component contains an acid. The components when combined, are combined in approximately equal weight proportions, so that only about one-half of the concentration of any particular ingredient within either component will be present when the components are combined and applied to the teeth, as by brushing. Both components are formulated with similar vehicle ingredients, with the significant exception being the presence of the bicarbonate and alkyl vanillyamide in the first component and the acid in the second component. This similarity of vehicle ingredients is to provide similar physical characteristics to promote similar rheology so that the two components are delivered simultaneously in the desired equal measure by extrusion from a dual compartmented tube or pump device.

The Bicarbonate Salt Component

The dentifrice component containing the alkali metal bicarbonate salt is stable and non-effervescent and contains from about 5 to about 15 percent by weight of the bicarbonate salt. It is preferred that the pH of the dentifrice when the components are mixed in the mouth, as by brushing, be from about 6.0 to about 7.4. To obtain this pH in the combined dentifrice, the quantity of bicarbonate in the first component is preferably from about 10 to about 12 percent by weight whereby the pH of the first component is from about 7.5 to 9.5 and preferably from about 8.5 to 9.0. This quantity of bicarbonate salt will, in the combined dentifrice, provide the desired pH and resulting effervescence, with the added benefit that the salty taste associated with bicarbonate salts is minimized.

Alkali metal bicarbonate salts used in the practice of the present invention, includes potassium bicarbonate and sodium bicarbonate; however, sodium bicarbonate is preferred. Sodium bicarbonate is a powder composed of relatively soft particles compared to most conventional abrasive particles used in toothpastes. The size of the sodium bicarbonate particles may vary from course to fine; it is preferred that they be largely below about 0.4 mm in diameter, with a major proportion by weight being below about 0.01 mm. in diameter.

Certain therapeutic ingredients, which are basic in nature and not compatible with the acidic dentifrice component are incorporated in the bicarbonate salt component of the dual component dentifrice of the present invention. Examples of such therapeutic ingredients include anti-tartar agents, such as sodium tripolyphosphate and tetrasodium pyrophosphate and anticavity agents such as sodium fluoride and sodium monofluorophosphate. These ingredients are incorporated in the dentifrice composition components at concentrations ranging from 0.5 to 8% by weight.

The Acidic Component

The acidic component of the dentifrice composition of the present invention, which is maintained physically separate from the bicarbonate salt component prior to combination and mixing, includes within the dentifrice vehicle an acidic compound such as malic acid, alginic acid, citric acid, succinic acid, lactic acid, tartaric acid, potassium bitartrate, acid sodium citrate, phosphoric acid, and acid phosphate, pyrophosphate salts, such as monosodium phosphate and disodium pyrophosphate. It is preferred that sodium dihydrogen phosphate, o-phosphoric acid, or sodium acid pyrophosphate be used individually or in combination. The amount of acid compound used ranges from about 1 to about 16% by weight of the acidic dentifrice component and preferably from about 2 to about 5% by weight, such that the pH of the acidic dentifrice component is from about 1.5 to about 4.5, and preferably from about 2.5 to about 3.5.

Dentifrice Vehicle Common to Both Components

In the preparation of both dentifrice components of the present invention, the respective acid or bicarbonate ingredient is incorporated within a pharmaceutically-acceptable vehicle suitable for use in the oral cavity, which contains water, humectant, surfactant and a polishing agent or abrasive.

The humectant is generally a mixture of humectants, such as glycerol, sorbitol and polyethylene glycol of a molecular weight in the range of 200–1000, but other mixtures of humectants and single humectants may also be employed. The humectant content within each of the two components is in the range about of 10% to about 30% by weight and preferably about 10 to about 20% by weight. The water content which is from about 20% to about 55%, and preferably from about 25 to 50% by weight.

Polishing agents or abrasives which may be present in both components of the dentifrice include sodium metaphosphate, potassium metaphosphate, tricalcium phosphate, dihydrated dicalcium phosphate calcined alumina and siliceous materials or combinations thereof. Preferred polishing agents include dicalcium phosphate and siliceous materials, such as silica and more preferably a precipitated amorphous hydrated silica, such as Zeodent 115, marketed by J.M. Huber Chemicals Division, Havre de Grace, Md. 21078, or Sylodent 783 Sylodent XWAA 300 available from Grace Davidson, Baltimore, Md. 21203.

Organic or inorganic thickeners may be included in the dentifrice of the present invention. Organic thickeners such as natural and synthetic gums and colloids may also be incorporated in the present invention. Examples of such organic thickeners include carrageenan (Irish moss), xanthan gum and sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Inorganic thickeners such as laponite are preferred, as well as amorphous silica compounds which function as thickening agents including, colloidal silica compounds available under tradenames such as Cab-o-sil fumed silica manufactured by Cabot Corporation and distributed by Lenape Chemical, Bound Brook, N.J., Zeodent 165 from J.M. Huber Chemicals Division, Havre de Grace, Md. 21078 and Sylox 15 from Grace Davidson, Baltimore, Md. 21203. Either inorganic or organic thickening agents, or combinations thereof, may be present in both components of the dentifrice in proportions of about 0.1 to about 10% by weight, preferably about 5 to about 8% by weight in each of the two components of the dentifrice.

Surface active agents or surfactants may be incorporated in both components of the present invention as an ingredient to aid in the thorough dispersion of the dentifrice throughout the oral cavity when applied thereto, as well as, to improve cosmetic acceptability and the foaming properties. The surface active agents which can be included within the vehicle of both components of the present invention include anionic, nonionic or amphoteric compounds, anionic compounds being preferred.

Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate.

Examples of water soluble nonionic surface active agents are condensation products of ethylene oxide with various hydrogen-containing compounds that are reactive therewith and have long hydrophobic chains (e.g., aliphatic chains of about 12 of 20 carbon atoms), which condensation products contain hydrophilic polyoxyethylene moieties, such as condensation products of poly (ethylene oxide) with fatty acids, fatty alcohols, fatty amides and other fatty moieties, and with propylene oxide and polypropylene oxides, e.g., Pluronic® materials such as Pluronic F127.

The surface active agent can be present in one or both components of the instant inventive compositions of the present invention at a concentration of about 0.5 to about 5.0% by weight, preferably about 1 to about 2% by weight of the particular component.

Linear molecularly dehydrated polyphosphate salts can be employed as anticalculus agents. They are well known, being generally employed in the form of their wholly or partially neutralized water soluble alkali metal (e.g. potassium or sodium3 or ammonium salts, and any mixtures thereof. Representative examples include sodium tripolyphosphate, monosodium triacid-, disodium diacid-, trisodium monoacid-, and tetrasodium-pyrophosphates, the corresponding potassium salts and the like. In the present invention, they can be employed in the oral compositions in approximate weight amounts of about 0.1 to about 3%, typically about 1 to about 2.5%, more typically about 1.5 to about 2%, especially about 2%. Preferred anticalculus agents are tetraalkali metal pyrophosphates such as tetrasodium and tetrapotassium pyrophosphates, and mixtures thereof.

Fluoride ions may also be included in the dentifrice compositions of the present invention to provide an anticaries effect. Among these materials are inorganic fluoride salts, such as soluble alkali metal fluoride salts, for example, sodium fluoride, potassium fluoride, sodium monofluorophosphate and sodium hexafluorosilicate. Alkali metal fluorides, such as sodium fluoride, sodium monofluorophosphate, sodium hexafluorosilicate and mixtures thereof, are preferred.

The amount of fluorine-providing salt is generally present in the oral composition at a concentration of about 0.0005 to about 3.0% by weight. Any suitable minimum amount of such salt may be used, but it is preferable to employ sufficient fluoride salt to release about 300 to 2,000 ppm, more preferably about 800 to about 1,500 ppm, of fluoride ion.

A striped dentifrice product may be obtained using the multicomponent dentifrice of the present invention, wherein colorants of contrasting colors are incorporated in each of the dentifrice components to be dispensed; the colorants being pharmacologically and physiologically non-toxic when used in the suggested amounts. Colorants used in the practice of the present invention include both pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The concentration of the dye in the dentifrice composition in an amount from about 0.0005 percent to about 2 percent by weight of the respective component.

To prepare each of the individual dentifrice components, generally the humectants e.g. glycerin, polyethylene glycol ingredients, are mixed with any organic thickener to form a first mix. A second mix of fluoride, sweetener and water (in the case of the bicarbonate first dentifrice component, only one-half of the formulation water is added at this point) is simultaneously prepared. For the acidic second component, the acid is added into this second mix. The first and second mixes are dispersed together in a conventional mixer until the mixture therein becomes a homogeneous gel phase. Into the gel phase are added any inorganic abrasive/polishing agent or thickener, including into the first component. For the basic component, the sodium bicarbonate is added as a second powders mix, following the abrasive powders mix. The alkyl vanillyamide compound is predissolved and added with the flavors. These ingredients are mixed until a homogeneous phase is obtained. Thereafter the flavor and surfactant ingredients are added and the ingredients mixed at high speed under vacuum of about 20–100 mm Hg. The resultant product is in each case a homogeneous, semi-solid, extrudable paste product.

The two component dentifrice composition of the present invention may be packaged in a suitable dispensing container in which the components are maintained physically separated and from which the separated components may be dispensed synchronously as a ribbon for application to a toothbrush. Such containers are known in the art. An example of such a container is a two compartment dispensing container having collapsible sidewalls, as disclosed in U.S. Pat. Nos. 4,487,757 and 4,687,663 wherein the container body is formed from a collapsible plastic web and is provided with a partition within the container body defining separate compartments in which the physically separated components are stored and from which they are dispensed through a suitable dispensing outlet.

The following examples are further illustrative of the present invention, but it is understood that the invention is not limited thereto. All amounts and proportions referred to herein and the appended claims are by weight.

EXAMPLE

The effervescent signal produced by the dual component dentifrice of the present invention derives from the evolution of carbon dioxide upon mixing of the alkaline pH paste (pH range 8–9) and the acid pH gel (pH range 2–4). Upon mixing, the dentifrice has an overall pH of approximately 6.8–7.25 when measured during gas evolution. A dual component dentifrice consisting of a bicarbonate dentifrice component (Component A) and an acid component (Component B) was prepared using the ingredients listed in Table I below wherein the naturally occurring alkyl vanillyamide, capsaicin, was incorporated in the bicarbonate Component A.

TABLE I

| Components Ingredients | A Weight % | B Weight % |
| --- | --- | --- |
| Glycerine (95%) | 13.00 | 10.0 |
| Sorbitol | — | 8.00 |
| Sodium lauryl sulfate | 3.00 | — |
| Betaine (30% soln.) | 2.00 | — |
| Pluronic F-127 | — | 1.50 |
| Xanthan gum | 0.7 | 0.6 |
| Laponite D | — | 0.6 |
| Flavor | 1.15 | 1.15 |
| Sodium fluoride | 0.486 | — |
| Sodium hexafluorosilicate | — | 0.239 |
| Titanium dioxide | 0.30 | — |
| Tetrasodium pyrophosphate | 0.60 | 0.00 |
| Sodium saccharin | 0.30 | 0.30 |
| Sodium bicarbonate | 11.75 | — |
| Silica thickener | 2.00 | 2.50 |
| Capsaicin (1.0% soln.) | 2.00 | — |
| Silica abrasive | 23.0 | 35.0 |
| o-Phosphoric acid (70% soln.) | — | 3.4 |
| Sodium acid pyrophosphate | — | 1.50 |
| Blue pigment | — | 0.0125 |
| Deionized water | QS | QS |

Component A was prepared by dispersing the formula quantities of xanthan gum and tetrasodium pyrophosphate in the glycerine and sorbitol, using a high speed bench top mixer until a homogenous first pre-mix formed; one-half of the formula quantity of water was then used to dissolve the formula quantities of the sodium fluoride and the sodium saccharin using the high speed bench mixer to form a homogenous second pre-mix; the balance of the water was then used to dissolve as much as possible of the sodium bicarbonate to form a third pre-mix; the first two pre-mixes were then mixed together using the high speed mixer to form a homogenous mixture and the third pre-mix was then added thereto and the mixing continued for about 15 minutes until a homogenous gel phase formed. This homogenous gel phase was transferred to a Ross type vacuum mixer and the formula quantities of the Zeodent 165 thickener and Zeodent 165 and Sylodent 783 abrasive were added thereto and the mixing continued under 30 mm of Hg vacuum for 15 minutes. The formula quantities of the remaining ingredients, capaicin, sodium lauryl sulfate and flavor were then added to the Ross type vacuum mixer and this complete mixture was mixed under 30 mm of Hg vacuum for 10 minutes.

Component B was prepared by dispersing the formula quantities of xanthan gum in the glycerine and sorbitol, using a high speed bench top mixer until a homogenous first pre-mix formed; one-half of the formula quantity of water was then used to dissolve the formula quantity of the blue pigment and the sodium saccharin using the high speed bench mixer to form a homogenous second pre-mix; the balance of the water was then used to dilute the formula quantity of o-phosphoric acid, sodium dihydrogen phosphate and sodium acid pyrophosphate to form a third pre-mix; the three pre-mixes were then mixed together using the high speed mixer to form a homogenous gel phase which was transferred to a Ross type vacuum mixer. Into this gel phase within the Ross type vacuum mixer was added the silica thickener and abrasive and this resulting product was mixed for 15 minutes under 30 mm of Hg vacuum. The formula quantities of the remaining ingredients, the Pluronic F-127 surfactant and flavor oils were then added to the Ross type vacuum mixer and this complete mixture was mixed under 30 mm of Hg vacuum for 20 minutes.

When Components A and B were combined and admixed $CO_2$ gas was evolved. The resultant dentifrice composition, designated "Dentifrice X" had a pH of 6.9 when diluted with three parts water.

The evolution of carbon dioxide gas was detected quantitatively by measuring the amount of gas bubbles generated upon mixing 0.5 parts of the acidic dentifrice Component B and 0.5 parts of the alkaline dentifrice Component A on a weight basis with 3 parts water at 37° C. The results of the gas evolution test are recorded below in Table III.

For purposes of comparison, an effervescent dentifrice composition consisting of alkaline and acidic Components C and D respectively were prepared using sodium bicarbonate and phosphoric acid ingredients in the separate components and without the presence of the capaicin. The ingredients of Components C and D are listed in Table II below.

TABLE II

| Component C | Weight % | Component D | Weight % |
|---|---|---|---|
| Sodium bicarbonate | 10.0 | Polyethylene glycol | 10.0 |
| Sodium saccharin | 0.60 | Phosphoric acid (85%) | 0.10 |
| Sodium fluoride | 0.486 | Glycerin | 30.0 |
| Sorbitol | 42.8 | Blue colorant (1%) | 0.7 |
| Titanium dioxide | 0.50 | Pluronic F-127 | 20.0 |
| Carboxy methylcellulose gum | 1.00 | Flavor | 0.3 |
| Zeodent-165 | 4.00 | Hydrogen peroxide (35%) | 4.286 |
| Zeodent-115 | 15.0 | Sodium saccharin | 0.10 |
| Flavor | 1.50 | FD & C Blue #1 (1% soln.) | 0.70 |
| Sodium lauryl sulfate | 3.00 | BHT | 0.03 |
| PEG-32 | 5.00 | | |
| Water | QS | Water | QS |

When components C and D were combined, $CO_2$ gas was evolved. The resultant dentifrice composition designated "Dentifrice Y", had a pH of 8.9. The procedure of the Example was repeated to determine the amount of the gas evolution from Dentifrice Y, which is recorded in Table III.

For purposes of further comparison, a commercial sensory dentifrice designated "Dentifrice Z" was also evaluated for gas evolution, which was a dual component, pump dispensed baking soda/fruit acid toothpaste in which one chamber of the pump contained weak organic and fruit acids and the other chamber contained bicarbonate salt. The ingredients listed on the package label were glycerine, water, Poloxamer 407, hydrated silica, sodium bicarbonate, PEG-32, sodium lauryl sulfate, flavor, saccharin, NaF, cellulose gum, Triclosan, zinc sulfate, pyrus malus, propylene glycol, citric acid, glycolic acid, malic acid and colorants.

The gas evolution from Dentifrice Z is also recorded in Table III below.

TABLE III

| Dentifrice | ml gas/30g dentifrice after 90 sec. |
|---|---|
| X | 81 |
| Y | 22 |
| Z | 10 |

The results recorded in Table III indicate that by analytically measuring the quantity of gas generated during mixing of the two adjacent streams for the dentifrice compositions being evaluated using conditions that simulate those experienced during brushing, the dentifrice composition of the present invention, Dentifrice X exhibited significantly greater levels of evolved gas, significantly influencing the perceived quantity of foam volume and hence mouthfeel sensations experienced during brushing in comparison to other prototypes.

The sensorial impact of Dentifrices X, Y and Z delivered during tooth brushing, were evaluated by a panel expert in sensory analysis (n=13) in a quantitative sensory study using a standard brushing evaluation. Each dentifrice composition was evaluated a total of two times by each panelist in a statistically balanced order. Results were evaluated statistically using analysis of variance and Tukey post-hocs where differences at the 90% confidence level were considered significant. The results are recorded below in Table IV.

TABLE IV

| | Dentifrice Composition | | |
|---|---|---|---|
| Sensory Signal | X | Y | Z |
| Particle size | 4.5 | 1.9 | 1.60 |
| Burn mouth | 3.0 | 2.8 | 3.50 |
| Fizz-tongue | 1.1 | 0.30 | 0.30 |
| Tingle-tongue | 1.8 | 0.40 | 0.40 |
| Fizz-mouth | 0.70 | 0.10 | 0.10 |
| Tingle-mouth | 0.90 | 0.30 | 0.20 | p =

The results recorded in Table IV indicate that the rapid generation of $CO_2$ gas, combined with the presence of capsaicin provide significantly better mouthfeel signals when compared to comparable dentifrice compositions formulated without the presence of capsaicin. The sensorial cue, the tingly or fizz sensation is an integral element in the delivery of a sensorally based effervescent sensation.

The presence of the alkyl vanillyamide species did not contribute to or cause excessive burn during use, further enhancing the sensory cues experienced during brushing.

What is claimed is:

1. A two component effervescent dentifrice composition, having a first dentifrice component containing an alkali metal bicarbonate and a naturally occurring alkyl vanillyamide maintained at a pH of about 7.5 to 9.5 and a second acid containing dentifrice component, maintained at a pH of about 1.5 to about 4.5, the first and second components being separated prior to use, wherein the reaction between the two components generates a carbon dioxide gas effervescent signal upon the combination and mixing of the components, the signal being enhanced by the presence in the combined components of the naturally occurring alkyl vanillyamide, the presence of which provides a unique and enhanced consumer measurable tingly or fizz mouthfeel sensation on the tongue and mouth during brushing instilling in the consumer a perception of enhanced product cleaning performance.

2. The composition of claim 1, wherein the alkali metal bicarbonate is sodium bicarbonate.

3. The composition of claim 1, wherein the second acid-containing dentifrice component contains phosphoric acid.

4. The composition of claim 1, wherein the alkyl vanillyamide is capsaicin.

5. The composition of claim 1 wherein the alkyl vanillyamide is present in the bicarbonate containing dentifrice component in the range of about 0.001 to about 1% by weight.

6. The composition of claim 1 wherein the mixed components have a pH in the range of about 6 to about 7.1.

7. A method for enhancing sensory signal from an effervescent dentifrice which comprises preparing a two component dentifrice; the first containing an alkali metal bicarbonate and naturally occurring alkyl vanillyamide maintained at a pH of about 7.5 to about 9.5 the second dentifrice component containing an acid component maintained at a pH of about 1.5 to 4.5 maintaining the first and second dentifrice components separate from each other until dispensed for application to teeth, whereby the two components when combined and admixed during brushing react to generate a carbon dioxide effervescent signal the presence of the alkyl vanillyamide providing an enhanced sensory signal.

8. The method of claim 7, wherein the alkali metal bicarbonate is sodium bicarbonate.

9. The method of claim 7 wherein the second acid-containing dentifrice component contains phosphoric acid.

10. The method of claim 7 wherein the vanillyamide is capsaicin.

11. The method of claim 7 wherein the vanillyamide is present I the bicarbonate dentifrice containing component in the range of about 0.001 to about 1.0% by weight.

12. The method of claim 7 wherein the mixed components have a pH in the range of about 6.0 to about 7.1.

* * * * *